United States Patent [19]

Jones et al.

[11] Patent Number: 5,066,587

[45] Date of Patent: Nov. 19, 1991

[54] GAS DRIVEN MICROPROJECTILE ACCELERATOR AND METHOD OF USE

[75] Inventors: Lawrence D. Jones, Portage; Paul T. Frey, Delton; David D. Gleason, Oshtemo Township, Kalamazoo County; Paula P. Chee; Jerry L. Slightom, both of Kalamazoo, all of Mich.

[73] Assignee: The Upjohn Company, Kalamazoo, Mich.

[21] Appl. No.: 471,216

[22] Filed: Jan. 26, 1990

[51] Int. Cl.$^5$ .................. C12N 15/89; C12M 1/00
[52] U.S. Cl. ................... 435/172.1; 435/172.3; 435/287; 935/53; 935/85
[58] Field of Search ............ 435/172.1, 172.3, 287; 935/53, 52, 85; 73/11-13, 167; 604/68, 70, 71, 131, 140, 141, 143; 124/56, 60, 71, 72, 73

[56] References Cited

U.S. PATENT DOCUMENTS

| 3,343,400 | 9/1967 | Rogers et al. | 73/12 |
| 3,404,599 | 10/1968 | Annis | 73/12 |
| 4,945,050 | 7/1990 | Sanford et al. | 435/172.1 |

FOREIGN PATENT DOCUMENTS 0270356  6/1988  European Pat. Off. .

OTHER PUBLICATIONS

Klein et al., "High-Velocity Microprojectiles for Delivering Nucleic Acids Into Living Cells", Nature, vol. 327 (May 7, 1987), pp. 70-73.

Klein et al., "Factors Influencing Gene Delivery Into Zea Mays Cells by High-Velocity Microprojectiles", Bio/Technology, vol. 6 (May 1988), pp. 559-563.

McCabe et al., "Stable Transformation of Soybean (Glycine Max) by Particle Acceleration", Bio/Technology, vol. 6 (Aug. 1988), pp. 923-926.

Marikawa et al., "Transient Expression of Foreign Genes in Plant Cells and Tissues Obtained by a Simple Biolistic Device", Applied Microbiology and Biotechnology, vol. 31 (1989), pp. 320-322.

Primary Examiner—David L. Lacey
Assistant Examiner—William H. Beisner
Attorney, Agent, or Firm—Flynn, Thiel, Boutell & Tanis

[57] ABSTRACT

A foreign substance, such as DNA, is injected into plant cells or tissue by a biological ballistical insertion technique. High pressure propellant gas is employed to accelerate the macroprojectile containing microprojectiles coated with the foreign substance. A movable macroprojectile stop mechanism is provided between an upper injection chamber and a lower sample-holding chamber so that multiple shots of macroprojectiles can be made without disrupting the vacuum in the lower chamber. The stop mechanism includes removable stopper plugs for stopping the macroprojectile. A vacuum seal is provided between the stop mechanism and the lower chamber.

7 Claims, 5 Drawing Sheets

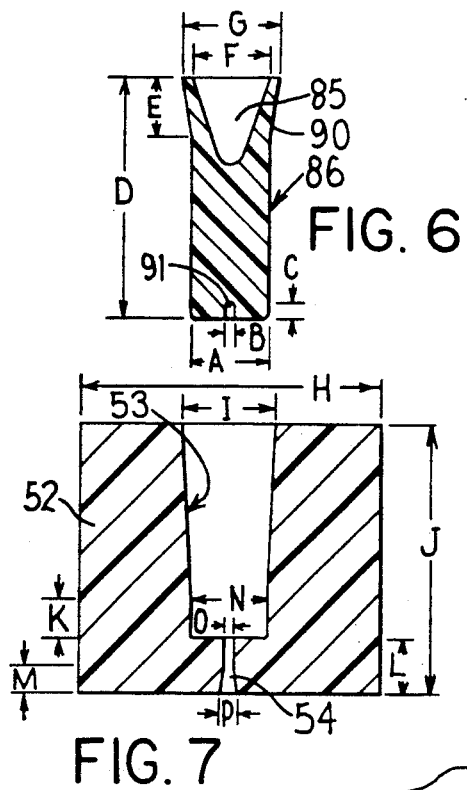
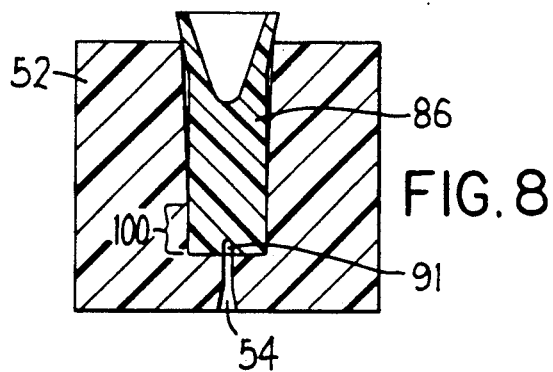
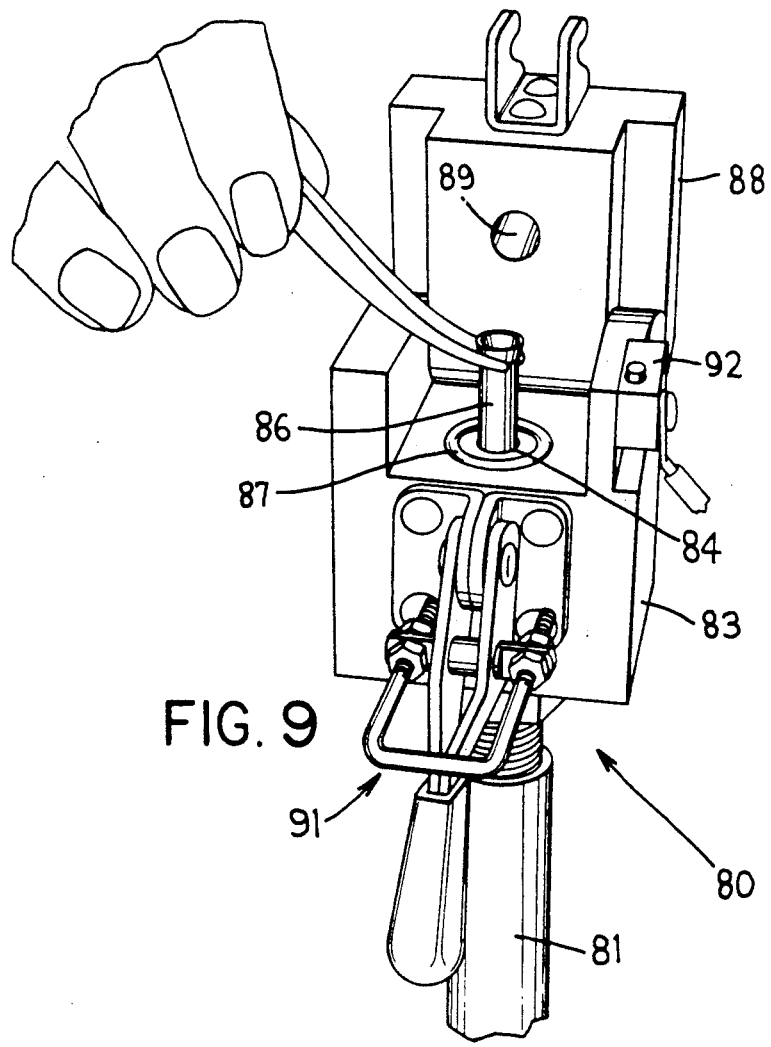

GAS DRIVEN MICROPROJECTILE ACCELERATOR AND METHOD OF USE

This invention relates to the genetic engineering of plants and, more particularly, to an apparatus and method for introducing foreign substances, such as DNA, into living plant cells or tissues by means of a gas-powered microprojectile accelerator. The accelerator is capable of effecting multiple shots, each consisting of a multitude of microprojectiles which are directed at the same or different cell or plant tissue targets.

DESCRIPTION OF THE PRIOR ART

The successful delivery of foreign substances, such as DNA, into cells or plant tissue using high-velocity microprojectiles was reported by Klein, T. M. et al, Nature, 327:70–73 (1987). Additional reports on related work are:

1. Klein, T. M., et al, Bio/Tech., 6:559-564;
2. McCabe, D. E., et al, Bio/Tech., 6:923-926; and
3. European Patent Office Publication No. 0270356.

In those methods, metal microprojectiles coated with the foreign substance, such as DNA, are either disposed on a macroprojectile which is accelerated by an explosion of gun powder or they are mounted on a carrier sheet and are accelerated by the shock waves created by a high-voltage electrical discharge. Although these methods are capable of transferring foreign substances, such as DNA, into living cells, they have some disadvantages which make them less than fully satisfactory. For example, in the method employing gun powder, unburned gun powder may build up in the apparatus which can create safety problems. Frequent cleaning of the apparatus will be necessary. Further, it is not possible to select and closely control the velocity of the macroprojectile or the speed of the spent gas. Cell damage can occur caused by an excessively high velocity of the microprojectiles when they strike the cells and/or by high-pressure gas impinging directly on the cells. Moreover, the prior methods are one-shot methods. It was not possible to fire multiple shots of the foreign substance at the same target or different targets in rapid succession. Previous attempts to effect multiple shots were not satisfactory because a substantially uniform vacuum was not maintained around the target.

Accordingly, it is an object of this invention to provide an improved microprojectile accelerator for use in the genetic engineering of plants, in which multiple shots each consisting of a multitude of microprojectiles, can be fired in close succession, directed at the same or different targets, without interrupting the substantially constant vacuum that is continuously applied on the target(s).

It is a further object of the invention to provide an improved microprojectile accelerator, as aforesaid, in which the macroprojectile is accelerated by gas pressure from a conventional pressurized gas supply and without using an explosive.

It is a further object of the invention to provide an improved microprojectile accelerator in which a rotatable table is provided for containing macroprojectile stopper plugs and a rotatable vacuum seal is provided between the table and the support for the target so that the accelerator can be fired several times in close succession while continuously maintaining a vacuum around the target.

It is a further object of the invention to provide an improved microprojectile accelerator in which the macroprojectiles are caught by replaceable plastic stopper plugs.

SUMMARY OF THE INVENTION

According to the invention, there is provided an apparatus and a method for injecting microprojectiles carrying a foreign substance, such as DNA, into living cells and tissues. The apparatus includes a housing or casing which is divided by a partition wall into upper and lower vacuum chambers. Separately openable doors are provided for separately opening and closing the chambers. The chambers are hermetically sealed when they are closed. An indexable, rotatable table is provided in the upper chamber. A sample holder is disposed in the lower chamber. Seal means are provided between the upper and lower chambers so that vacuums can be separately maintained in those chambers. The table has a plurality of circumferentially spacedapart pockets which are adapted to receive removable macroprojectile stopper plugs. Means are provided to index the table so that the stopper plugs are moved through a plurality of angularly spaced-apart positions. The table is releasably locked in position between each indexing step. A gas-pressure operated gun is vertically aligned with one of the positions of the table so that firing of the gun will direct the macroprojectile into the stopper plug at that position. A multitude of microprojectiles are deposited on the forward end of the macroprojectile. A passage extends from the bottom of the pocket at said position into the lower chamber. When the macroprojectile is stopped by said stopper plug, the microprojectiles will be dislodged from the macroprojectile and will continue to move through the passage into the lower chamber at a high velocity so as to bombard and penetrate the sample in the lower chamber.

BRIEF DESCRIPTION OF THE DRAWINGS

In the accompanying drawings:

FIG. 6 is a central sectional view through a macroprojectile that is useful in the invention;

FIG. 7 is a sectional view through a stopper plug for use in the invention;

FIG. 8 is a sectional view of the macroprojectile and stopper plug after the macroprojectile has been impelled into the recess in the stopper plug; and FIG. 9 is a perspective view of the breech block portion of the gun.

DETAILED DESCRIPTION OF THE PREFERRED EMBODIMENT

Figure 1:
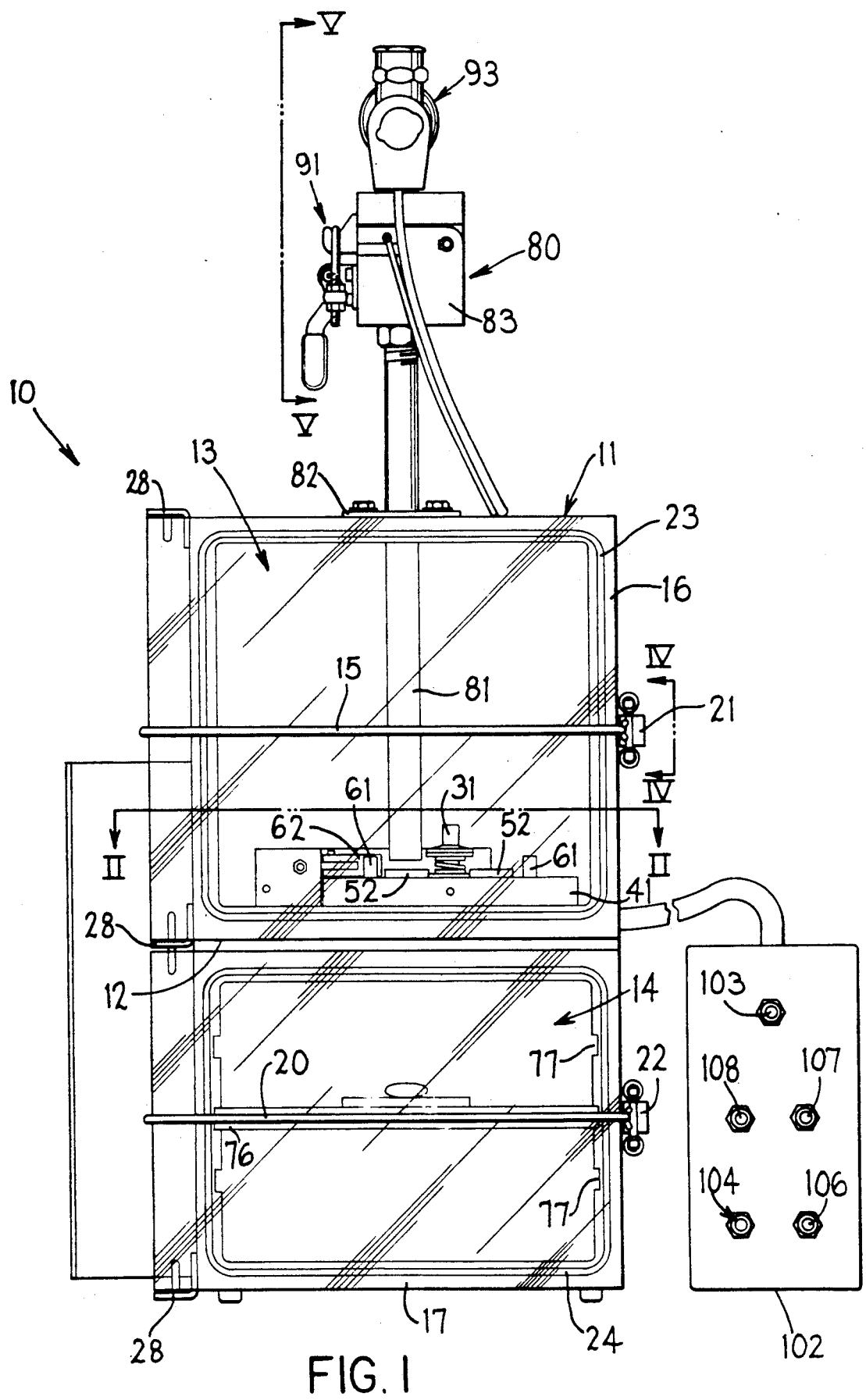
FIG. 1 is a front view of an apparatus according to the present invention.

Referring to FIG. 1, the projectile acceleration apparatus 10, according to the invention, comprises a housing 11 having top, bottom, side and back walls defining an enclosure which is open along the front side thereof.

A horizontal partition wall 12 divides the enclosure into an upper chamber 13 and a lower chamber 14. The open sides of the chambers 13 and 14 are releasably closed by two separate rectangular doors 16 and 17. The doors 16 and 17 are hingedly mounted on the housing 11 by means of hinges 28. Cables 18 and 19 (FIGS. 2 and 3) are secured at corresponding one ends thereof to one of the sidewalls of the housing. The cables 18 and 19 extend through tubes 15 and 20 which are attached to the front sides of doors 16 and 17, respectively, and extend crosswise thereof. The other ends of the cables 18 and 19 are connected to latches 21 and 22 so that the doors 16 and 17 can be separately releasably latched shut and can be separately opened when the need arises.

Figure 2:
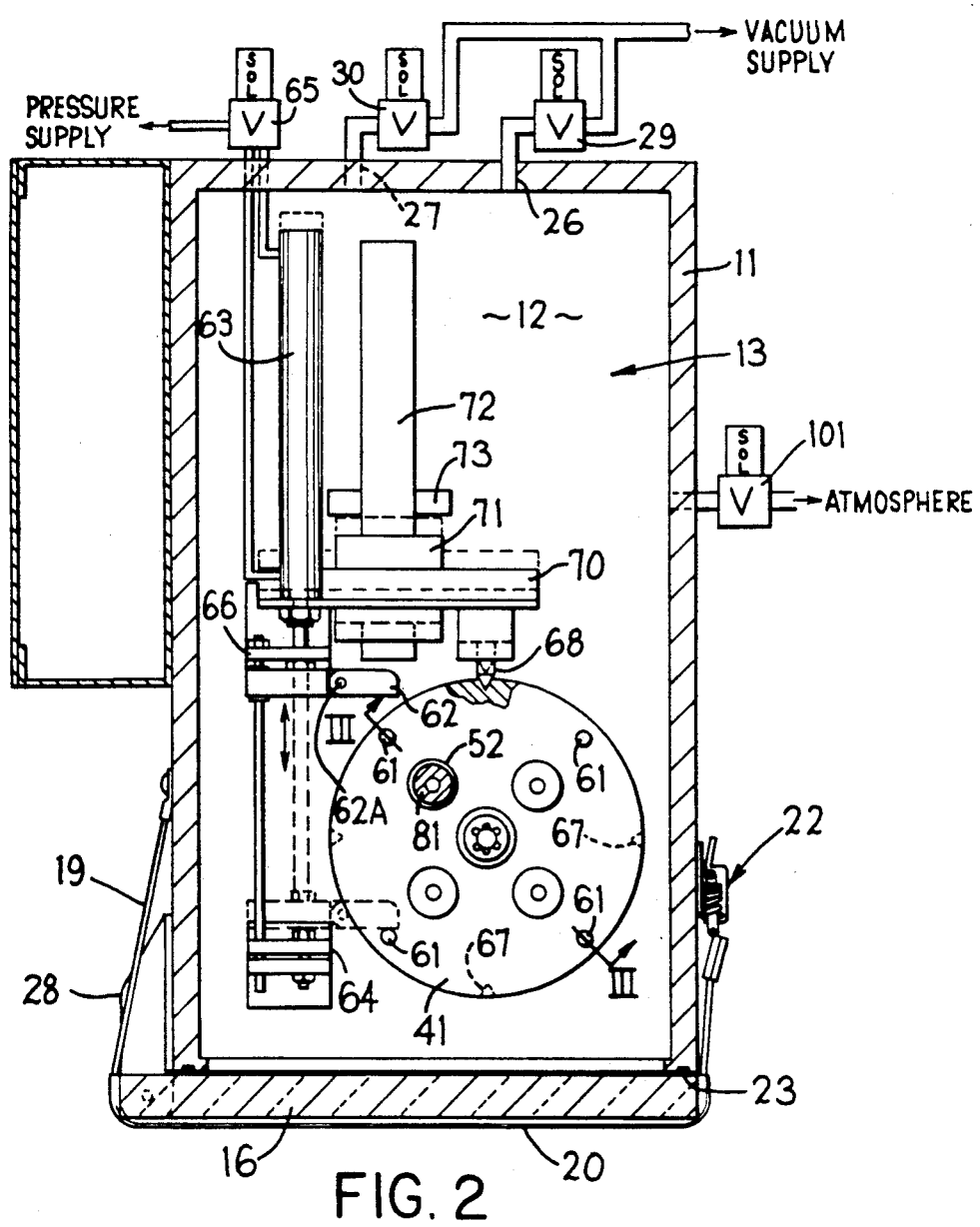
FIG. 2 is a sectional view taken along the line II—II of FIG. 1.
Figure 4:
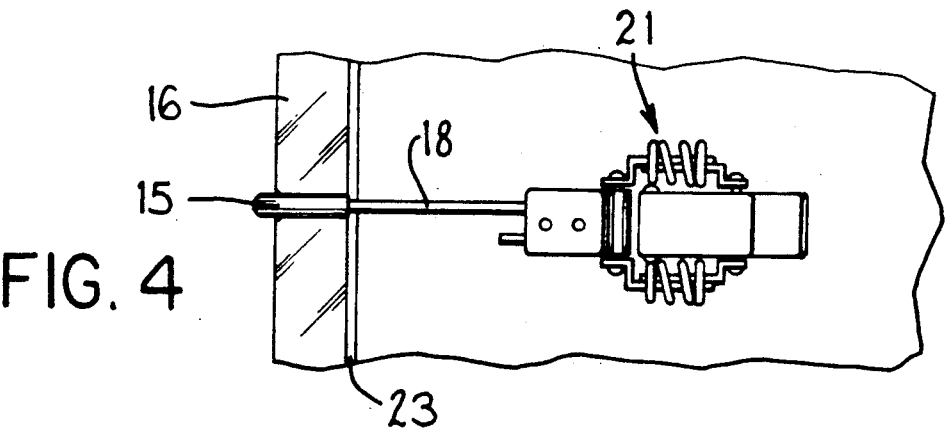
FIG. 4 is a partial side view taken along the line IV—IV of FIG. 1.

Referring to FIGS. 1, 2 and 4, gasket means, such as O-rings 23 and 24, encircle the open sides of chambers 13 and 14 and are adapted for sealing engagement with the doors 16 and 17 so that the chambers 13 and 14 are hermetically sealed when the doors 16 and 17 are latched shut. Preferably, the doors 16 and 17 are made of a suitable transparent material, such as poly(methylmethacrylate), so that the interiors of the chambers can be viewed by users of the apparatus while the doors are closed.

Conduits 26 and 27 are provided in the back walls of the chambers 13 and 14 and are connectable through solenoid valves 29 and 30, respectively, to a vacuum source, such as a vacuum pump, so that the chambers can be placed under vacuum independently of each other.

Figure 3:
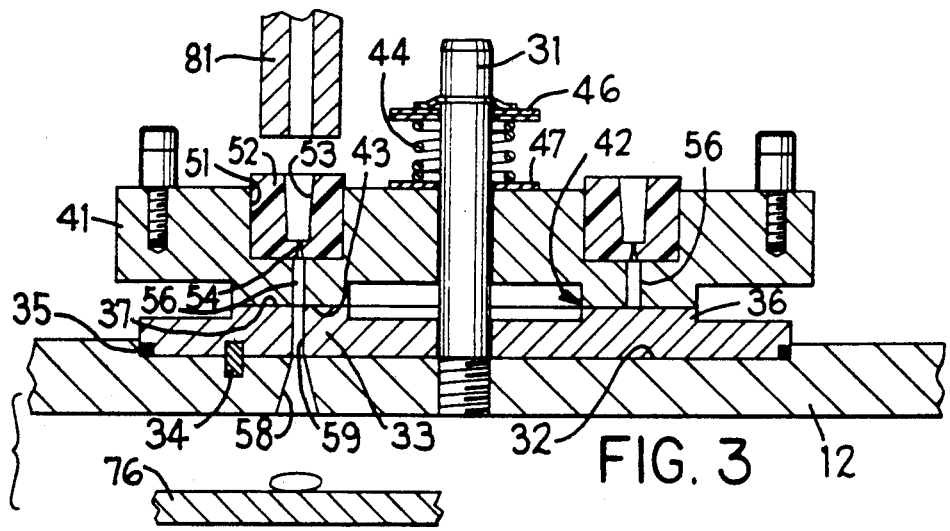
FIG. 3 is a sectional view taken along the line III-—III of FIG. 2.

Referring to FIG. 3, an upright axle 31 is disposed in the upper chamber 13 and it has a threaded lower end which is threaded into a threaded opening in the partition wall 12. The upper surface of the partition wall 12 has a shallow circular recess 32 therein, the center of which is coaxial with the axle 31. An annular support plate 33 encircles the axle 31, its lower portion is received in the recess 32 and its upper portion projects above the upper surface of partition wall 12. The lower portion of the peripheral surface of the support plate 33 has an annular notch that contains an 0-ring 35 so that the support plate 33 is sealed in the recess 32 to prevent leakage of gas therebetween. A locater pin 34 is provided to accurately position the support plate 33 in the recess 32 and hold it against rotation around the axle 31. An upwardly raised annular land 36, which is coaxial with the axle 31, projects upwardly from the upper surface of support plate 33. The land 36 has an upwardly facing, annular, perfectly flat, precision-finished, seal face 37 which is oriented at a right angle to the axis of axle 31.

An annular table 41 is coaxially mounted for stepwise, arcuate movement about the axis of the axle 31. The table 41 has a downwardly projecting annular land 42 which has a downwardly facing, annular, perfectly flat, precisionfinished, seal face 43 which is oriented at a right angle to the axis of axle 31 and which sealingly and slidably engages the seal face 37 on the support plate 33 whereby to provide a running seal between table 41 and support plate 33.

A coil spring 44 encircles the upper portion of the axle 31 and bears at one end against an upper spring retainer 46 which is mounted on and is fixed against axial movement with respect to the axle 31. The lower end of the coil spring 44 bears against a bearing plate 47 which is disposed on the upper surface of the table 41. The table 41 is thereby resiliently urged downwardly by the spring 44 so that the seal faces 37 and 43 are maintained in sealing, sliding contact with each other. The chambers 13 and 14 are sealed from each other except as discussed below.

The table 41 has a series of upwardly opening, evenly circumferentially spaced-apart pockets 51 therein, there being four pockets in the illustrated embodiment of the invention. A removable, macroprojectile stopper plug 52 is disposed in each of the pockets 51. The stopper plug 52 has a central cavity 53 of inverted frusto-conical shape provided therein and opening upwardly into the chamber 13. A narrow passage 54 extends downwardly from the bottom wall of the cavity 53 and it in turn communicates with a downwardly extending passageway 56, of larger diameter, which passageway extends to and through the seal face 43 of the land 42 of the table 41.

A single, frusto-conical orifice 58 is provided through the partition wall 12. The orifice 58 communicates with and constitutes an extension of a passage 59 that extends through the support plate 33 from the seal face 37 thereof through the bottom of the support plate 33. There is only one passage 59 and orifice 58. The upper end of the passage 59 is adapted to communicate with the lower end of only one of the passageways 56 at a time, when that one passageway 56 is in vertical alignment with the passage 59 as shown in the lefthand part of FIG. 3. At that time, the lower ends of the other three passageways 56 are sealed by the seal face 37.

The table 41 has four, equally circumferentially spaced-apart pins 61 fixed thereto and extending upwardly therefrom. A reciprocable pusher 62 is adapted to engage each of the pins in succession so that each forward reciprocation of the pusher 62 toward the door 16 will move the table 41 through an arc of 90 degrees, counterclockwise as appearing in FIG. 2, relative to the axle 31. The pusher 62 is pivotally mounted at pivot point 62A so that it can pivot out of the way, clockwise in FIG. 2, when it passes the next following pin 61 during the return stroke of the pusher. The pusher 62 is resiliently urged by a spring (not shown) into the solid line position shown in FIG. 2 so that the pusher will be in position for engagement with the next one of the pins 61 to be moved. The pusher 62 is reciprocated by a piston and cylinder device 63. Stationary stops 64 and 66 are provided to limit movement of the pusher 62 in both directions. A solenoid valve 65 is provided to control reciprocation of the pusher 62.

The table 41 has four equally circumferentially spaced-apart alignment pin recesses 67 provided in the periphery thereof. A reciprocable alignment pin 68 is releasably receivable in the adjacent one of said recesses 67 in order to releasably lock the table 41 in a selected position. The alignment pin recesses 67 are so arranged with respect to the pockets 51 and the stopper plugs 52 that when the alignment pin 68 is received in one of the recesses 67, one of the openings 56 will be in vertical alignment with the opening 59 in the support plate 33 and the orifice 58 in the partition wall 12, as shown in the lefthand portion of FIG. 3.

The alignment pin 68 and the cylinder 63 and associated parts, including the pusher 62, are mounted on a common support 70 having a collar 71 which is slidably mounted on and guided by a guide element 72 attached to the partition wall 12. A stop collar 73 is mounted on the guide element 72 to limit rearward movement of the support 71 and the parts mounted thereon to the broken line position shown in FIG. 2. In the solid line position shown in FIG. 2, the alignment pin 68 extends into the adjacent recess 67, and the table 41 therefore cannot rotate. When it is desired to rotate the table 41, the valve 65 is actuated to supply gas pressure to cylinder 63 and thereby the pusher 62 is pushed against the adjacent stop 61 and exerts force on it. Since the table 41 cannot rotate until the alignment pin 68 is withdrawn from the recess 67, the force is translated to move the support 70 backwardly until pin 68 leaves the recess 67. The support 70 and the piston and cylinder assembly 63 are moved away from the table 41 until the alignment pin 68 is moved out of the recess 67, to the position shown by broken lines in FIG. 2. Then, continued supply of gas pressure to the piston and cylinder 63 will advance the piston rod whereby to index the table 41 through an arc of 90° until the pusher 62 abuts against the stop 64 as shown by broken lines in FIG. 2. In this way, the table 41 receives intermittent arcuate motion from the piston and cylinder device 63. When the valve 65 is actuated to reverse the flow of gas to the cylinder, first the support 70 and associated parts are moved the solid line position in FIG. 2 whereby to lock the table 41 against movement and then the piston moves to move the pusher 62 to its solid line position against the stop 66.

A horizontal sample support 76 is disposed in the lower chamber 14. In the illustrated embodiment, the opposing sidewalls of the lower chamber 14 have three vertically spaced-apart sets of slots 77 so that the support 76 can be located at any one of three vertically spaced-apart positions in the lower chamber 14, as needed to meet the required experimental conditions.

An upright tube defining the barrel 81 of a macroparticle gun 80 extends upwardly from a position closely vertically spaced above the upper end of the stopper plug 52 that is in the firing position wherein one of the passages 56 is vertically aligned with the passage 59 and orifice 58, as shown in the lefthand portion of FIG. 3. The gun barrel 81 extends through the top wall of the housing 11. A flange 82 is mounted on the gun barrel 81 for securing the gun barrel to the top wall of the housing. Referring to FIG. 9, a breech block assembly comprising a breech 83 and a breech block 88 is mounted on the upper end of the gun barrel 81. The breech 83 has a bore 84 extending therethrough and communicating with the central opening in the gun barrel 81. The bore 84 defines a receptacle for holding a macroprojectile 86. A sealing ring 87 encircles the upper end of the bore 84. The breech block 88 is pivotally mounted on the breech 83 and it is adapted to be pivoted from the open position thereof shown in FIG. 9 into a closed position shown in FIGS. 1 and 5, in which the breech block 88 closes the upper end of the bore 84 so that no gas can leak between the opposing surfaces of the breech 83 and the breech block 88. A passage 89 is provided through the breech block 88 and that passage is adapted to be in registry with the bore 84 when the breech block 88 is closed. A toggle-type latch 91 is provided for releasably locking the breech block 88 in closed position. A switch 92 is provided for giving a signal when the breech block 88 is closed and the latch 91 is locked.

Figure 5:
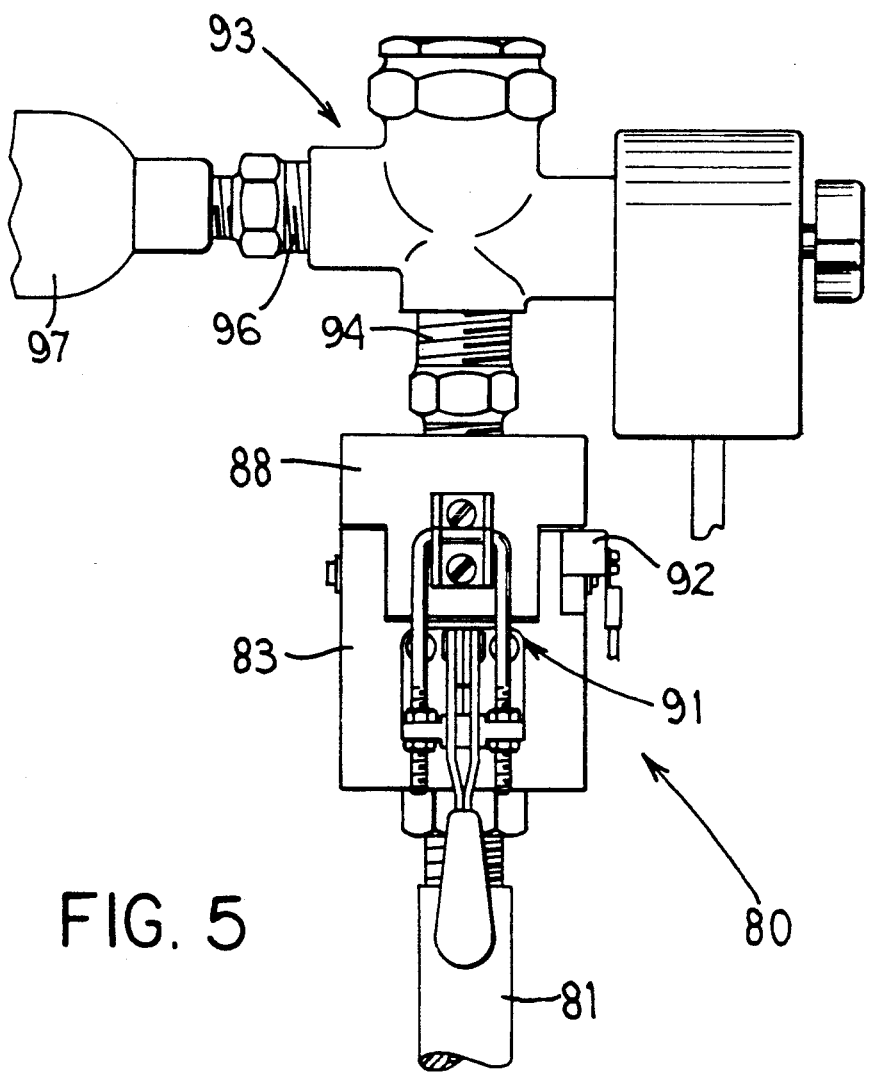
FIG. 5 is a partial side view taken along the line V—V of FIG. 1.

Referring to FIG. 5, a solenoid valve 93 has a port 94 which is connected to the passage 89 in the breech block 88. Another port 96 of the solenoid valve is connected to an accumulator vessel 97 which is charged using an external supply of high-pressure propellant gas, such as air or nitrogen. The accumulator vessel 97 is selected so that its exit port closely matches the internal port size of the solenoid valve 93. This matching of port sizes ensures the maximum rate of pressure exchange between the accumulator vessel 97 and the gun barrel 81. When the solenoid valve 93 is open, high-pressure gas flows through the port 94 and passage 89 into the bore 84 whereby to cause the macroprojectile 86 to be blown downwardly through the gun barrel 81 at a high velocity.

The use of high pressure propellant gas for firing the macroprojectile provides a number of significant advantages in comparison with the use of a firing system relying on explosive charges. In particular, the use of the high-pressure gas is safer, it permits the velocity of the macroprojectile to be controlled by controlling the pressure of the gas that is applied to the microprojectile 86, no heat is generated by the firing of the gun, the propellant gas can be changed in order to meet the required experimental conditions and damage of cells is minimized because the high-pressure gas is operative to effect selfsealing of the macroprojectile 86 in the stopper plug 52, as will be described hereinbelow.

Referring to FIG. 6, the macroprojectile 86 is a substantially circular plug having an inverted frusto-conical cavity 85 in its upper end and defining upwardly flaring sidewalls 90. The bottom wall of the macroprojectile 86 has a small centrally located dimple 91 therein for receiving the microprojectiles. The microprojectiles are very small particles of an inert metal, such as gold or tungsten. The foreign substance, such as DNA, is directly adsorbed on the surfaces of the inert metal particles. The diameter of the microprojectiles is very small, such as from about 0.6 to about 2.4 micrometers. Further, the total volume of the microprojectiles is very small in order to minimize scattering of the cell material of the cells or tissue being treated. For example, the total microprojectile volume can be from about 1.5 to about 2.5 microliters.

When the solenoid valve 93 is opened, the macroprojectile 86 will be accelerated to a high velocity and will be blown down the gun barrel 81. The lower portion of the macroprojectile 86 is sized so that it is freely vertically slidably receivable through the upper portion of the opening 53 of the stopper plug 52, but the lower portion of the macroprojectile has an interference fit with the lower portion of the opening 53 of the stopper plug 52. The macroprojectile 86 will be driven downwardly at a high speed until it bottoms in the opening 53. When the macroprojectile 86 bottoms in the opening 53, the microprojectiles in the dimple 91 will be dislodged therefrom and will flow downwardly at a high speed through passage 54, passageway 56, passage 59 and orifice 58 into the chamber 14 and thence they will strike the sample on the horizontal support 76. Many of the microprojectiles, which will be moving at a high velocity, will penetrate the cell walls of the sample material and will deliver the foreign substance, such as DNA, thereinto. In a presently preferred embodiment of the invention, the macroprojectile 86 is made of polyethylene and it has the following dimensions, referring to FIG. 6:

A = 0.250 inch
B = 0.040 inch
C = 0.050 inch
D = 0.750 inch
E = 0.200 inch
F = 0.225 inch
G = 0.265 inch The stopper plug 52 is made of polycarbonate and it has the following dimensions, referring to FIG. 7:

H=0.998 inch
I=0.300 inch
J=0.875 inch
K=0.125 inch
L=0.1875 inch
M=0.095 inch
N=0.250 inch
O=0.040 inch
P=0.080 inch The bottom face of the stopper plug 52 and the opposed end wall of the recess 53 are both ground flat and smooth so that a vacuum-tight seal can be achieved therebetween. The zone 100, whose size is substantially indicated by the dimensions N and K, is the macroprojectile seal zone in which the forward end portion of the macroprojectile 86 will be in substantially fluid-tight sealing relationship with the internal wall of the stopper plug 52, as shown in FIG. 8. When the macroprojectile seal zone 100 is established, the lower chamber 14 is completely isolated from the upper chamber 13 and the vacuum in the lower chamber 14 will not be disturbed even if the pressure in upper chamber 13 varies. The tail or upper end of the macroprojectile 86 is flared to assure a gas-tight seal when it is moving through the gun barrel 81 and when it is disposed in the central recess 53 in the stopper plug 52, as shown in FIG. 8.

The apparatus of the present invention is capable of effecting multiple shots of different macroprojectiles without interrupting the lower chamber vacuum. The rotating vacuum seal defined by seal faces 37 and 43 allows the table 41 to be advanced while substantially continuously maintaining vacuum in the lower chamber 14. This is necessary because the vacuum in the upper chamber is temporarily disrupted when the gun is fired and if the isolation of the lower chamber 14 from the upper chamber 13 were not maintained at this time, gas could enter the lower chamber 14 and disrupt the sample. When the table 41 is indexed from one position to the next, the upper chamber 13 will be in communication with the lower chamber 14 for the limited period of time between (1) the time when the passageway 56 of the next position is in communication with the passage 59, and (2) the time when the gun is next fired. This will normally be a very short time period and during this period vacuum will be applied in both chambers so that the desired vacuum conditions will not be disrupted. It is during firing of the gun 80 that significant pressure fluctuations can occur in the upper chamber 13 and when this happens the lower chamber 14 is isolated from the upper chamber 13.

A solenoid valve 101 is connected to the lower chamber 14 so that the lower chamber can be vented to the atmosphere at a selected time during the operation.

Figure 10:
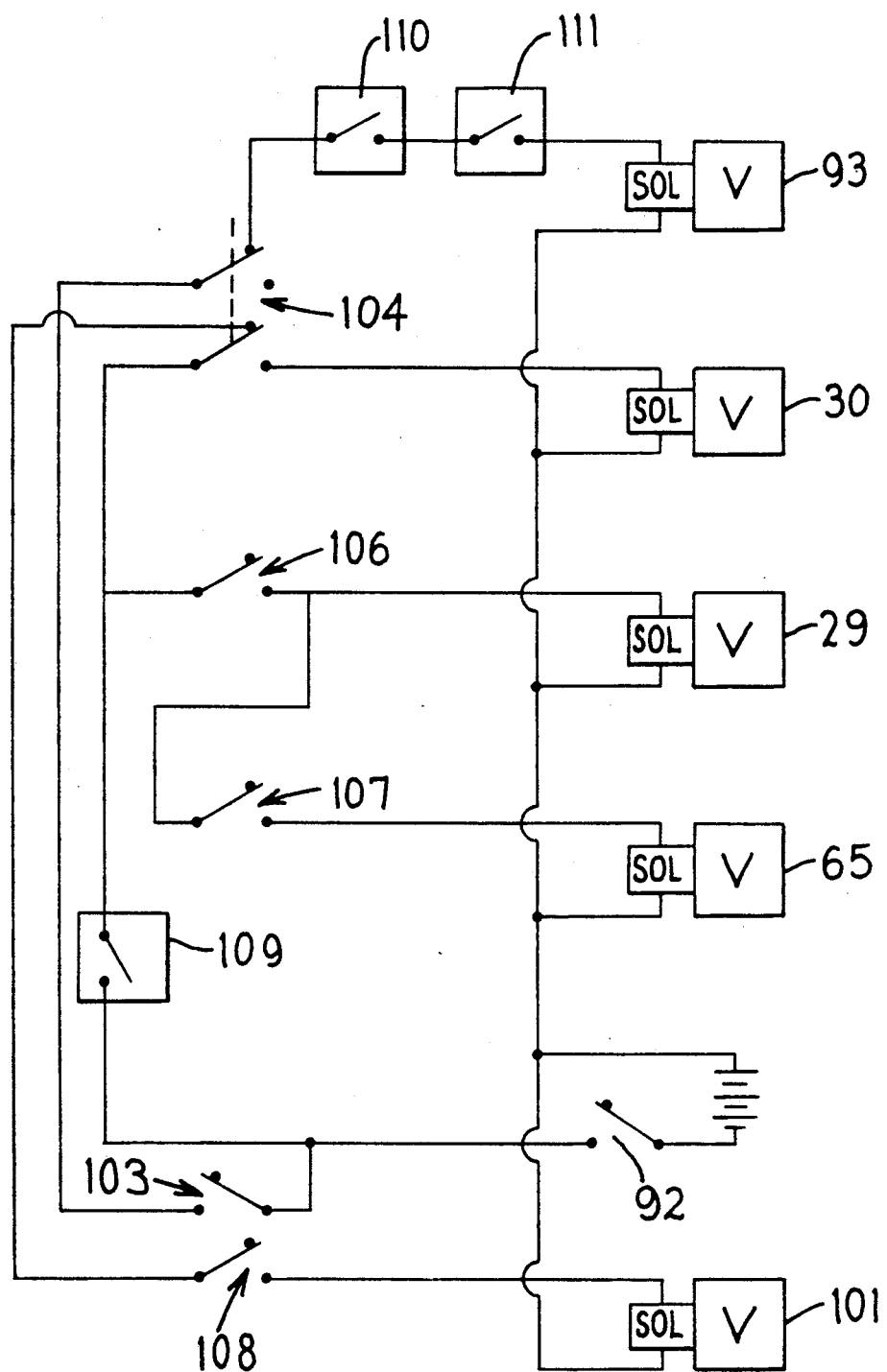
FIG. 10 is a schematic circuit diagram of the manual control circuit for the apparatus.

A manual control panel 102 (FIG. 1) includes a switch 103 for controlling the solenoid valve 93 effective for firing the gun, a switch 104 for controlling solenoid valve 30 effective for applying vacuum in the lower chamber 14, a switch 106 for controlling solenoid valve 29 effective for controlling vacuum in the upper chamber 13, a switch 107 for controlling solenoid 65 effective for controlling supply of gas to cylinder 63 and a switch 108 for controlling solenoid valve 101 effective for venting the lower chamber 14. The schematic circuit diagram is presented in FIG. 10.

OPERATION

For purposes of convenience in description, the operation of the apparatus will be described with reference to a manual operation in which application of vacuum to the chambers 13 and 14, supply of pressure fluid to cylinder 63, and supply of high pressure gas to the gun 80 are controlled by manually operated switches 103, 104, 106, 107 and 108 and vacuum interlocks 109 and 110 in the lower chamber 14, and vacuum interlock 111 in upper chamber 13. Vacuum interlock 109 is adjusted to trip or close at approximately 10 inches of mercury, whereas vacuum interlocks 110 and 111 are adjusted to trip or close at about 27 inches of mercury. It will be understood, however, that the operation of the apparatus can be controlled by means of a conventional programmable controller so as to make the operation and sequencing of the switches substantially automatic.

In preparing the apparatus for operation, the appropriate number of stopper plugs 52 is disposed in the cavities 51 in the table 41. The apparatus can be used for effecting single or multiple shots and, therefore, the number of plugs 52 used is equal to the intended number of shots to be made in the experiment. Further, the sample support shelf 76 is placed in the appropriate guide slots 77 in the lower chamber 14 and the sample to be treated is placed on that shelf.

The dimple 91 in the forward end of each of the macroprojectiles 86 to be used is loaded with the microprojectile material, that is, the small inert metal particles having the foreign substance, such as DNA, adsorbed thereon. The first macroprojectile 86 is then loaded into the bore 84 with the dimple end facing downwardly. The breech block 88 is then closed and the latch 91 is secured to make the gun 80 ready for firing. This also closes the switch 92.

The cell or tissue sample to be treated is placed on the shelf 76 in substantial vertical alignment with the lower end of the gun barrel 81 and with the orifice 58.

The doors 16 and 17 are then closed and latched to thereby hermetically seal the chambers 13 and 14. Then the switch 104 is closed to open the valve 30 that controls application of vacuum to the lower chamber 14 and a suitable vacuum, such as about 27 inches of mercury, is drawn in the lower chamber 14. After a predetermined delay time, for example, five seconds, the switch 106 is closed to open the valve 29 that controls application of vacuum to the upper chamber 13 and a suitable vacuum, such as 27 inches of mercury, is drawn in the upper chamber 13. The delay time is provided to enable the vacuum interlock 109 to operate. This ensures that vacuum cannot be applied in the upper chamber 13 before it is applied in the lower chamber 14. After both chambers 13 and 14 have reached their maximum vacuums, as indicated by vacuum gauges, then the switch 104 is opened, the valve 30 is closed and the vacuum source is disconnected from the lower chamber 14. Vacuum will be maintained in the lower chamber 14. Lower chamber 14 is isolated from the vacuum source and the upper chamber 13, at this time, so that gas pulses that may occur in the upper chamber during the firing of the macroprojectile 86 will not affect the pressure in the lower chamber 14. If the valve 30 were to be open during firing, a gas pulse or pulses might travel through valve 29 to the vacuum system and thence through valve 30 to the lower chamber 14 and thereby disrupt or scatter the sample.

The switch 103 is then closed to open the solenoid valve 93, through the closed contacts of vacuum interlocks 110 and 111, to release a measured volume of high pressure propellant gas through the passageway 89 into the bore 84, thereby forcing the macroprojectile 86 through the barrel 81 at a high velocity. When the macroprojectile 86 is received in the stopper plug 52 and the macroprojectile seal zone 100 is formed, a hermetic seal is formed between the chambers 13 and 14. At the same time that the seal is being formed, the microprojectiles pass through passage 54, passageway 56, passage 59 and orifice 58, and are injected into the target sample. Then the switch 104 is closed to open the valve 30 for applying vacuum to the lower chamber 14 so that the lower chamber is maintained under vacuum during the following step. Then the switch 106 is opened to close the valve 29 and disconnect the vacuum supply to the upper chamber 13 and the upper chamber 13 is vented to the atmosphere. Then the breech block 88 is opened, another macroprojectile 86 is placed in the bore 84, following which the breech block 88 is closed and latched. Then the switch 106 that controls the application of vacuum to the upper chamber is turned on. When maximum vacuum has been reestablished in the upper chamber, then the switch 107 is closed to open the valve 65 thereby to supply gas to the cylinder 63 and thereby index the table 41 to advance another stopper plug 52 into alignment with the gun barrel 81. Then the switch 104 is opened to close valve 93, the vacuum source is disconnected from the lower chamber 14 and the gun 80 is fired as described above.

After all of the injections of microprojectiles have been made in the above-described fashion, the upper chamber 13 is returned to atmospheric pressure, the lower chamber 14 is returned to atmospheric pressure by closing the switch 108 and thereby opening valve 101, the doors 16, 17 are opened, the sample is removed and the stopper plugs 52 containing spent macroprojectiles 86 are removed.

All of the injections of microprojectiles can be carried out without breaking the vacuum in the lower chamber. The existence of continuous vacuum in the lower chamber affects the velocity of the microprojectiles and their ability to deliver the foreign substance into the cells. In general, the higher the vacuum that is present in the lower chamber, the larger will be the number of units of DNA that will be contained in the cells after the bombardment.

The invention contemplates such changes or modifications as lie within the scope of the appended claims.

The embodiments of the invention in which an exclusive property or privilege is claimed are defined as follows:

1. Apparatus for injecting microprojectiles into a sample, comprising:
    a housing having wall means defining a first vacuum chamber and a second vacuum chamber, said first and second vacuum chambers being separately openable with respect to each other;
    a movable stop device in said first vacuum chamber, said stop device having a plurality of spaced apart recess means for receiving macroprojectiles;
    means for moving said stop device so as to move said plurality of recess means through a series of positions;
    passage means for providing flow communication between one of said recess means at one of said positions and said second vacuum chamber;
    a gun extending through said first chamber and aligned with said one recess means for driving a macroprojectile at a high velocity into said one recess means so that the macroprojectile seals said one recess means from gas and microprojectiles are dislodged from the forward end of the macroprojectile and flow through said passage means and bombard a sample in said second vacuum chamber;
    relatively movable sealing means for providing a hermetic seal between said first and second vacuum chambers when said passage means is closed and said stop device is moved in said first vacuum chamber; and
    a sample holder in said second vacuum chamber and disposed in alignment with said one recess means.

2. An apparatus as claimed in claim 1 which further includes a source of pressurized gas in communication with said gun through a valve for controlling supply of gas to said gun, said gun including a breech block and a gun barrel, said breech block having a bore for supplying gas to drive the macroprojectile through said gun barrel.

3. An apparatus as claimed in claim 1 wherein said movable stop device is a rotatable table comprising a series of circumferentially spaced-apart pockets and a stopper plug removably received in each of said pockets, said stopper plug and each of said pockets being constructed so as to define each of said recess means, each of said recess means having an interference fit with the macroprojectile whereby the macroprojectile seals each of said recess means and prevents flow of gas through said passage means.

4. An apparatus as claimed in claim 1, wherein said movable stop device is a rotatable table and said sealing means comprises a pair of relatively rotatable seal elements having precisionfinished, flat seal faces in sealing sliding contact with each other.

5. Apparatus for injecting microprojectiles carrying a foreign substance into living cells and tissue, comprising:
    a housing defining an enclosure, said housing having an internal partition wall dividing the interior of said housing into an upper chamber and a lower chamber, releasably lockable wall means for selectively and individually closing and hermetically sealing said chambers;
    a rotatable table in said upper chamber, said table having a series of circumferentially spaced-apart pockets therein and a macroprojectile stopper plug removably disposed in each of said pockets, said macroprojectile stopper plug having an enlarged central cavity which opens upwardly through the upper surface of said stopper and a narrow passage which extends from the bottom of said cavity through the bottom of said stopper plug and an opening provided in the bottom of each of said pockets;
    drive means for effecting stepwise indexing movement of said pockets through a series of circumferentially spaced-apart positions;
    a macroprojectile gun comprising an upright gun barrel extending upwardly from a position close to and located directly above one of said positions in vertical alignment with the macroprojectile stopper plug at said one position through said upper chamber to a location outside housing, a breech block assembly mounted on the upper end of said barrel and having an internal bore constructed so as to hold a macroprojectile, a breech block for closing the upper end of said internal bore, said breech block having a gas supply passage therethrough and communicating with the upper end of said internal bore, and a valve in communication with said gas supply passage for controlling flow of gas from a supply thereof through said gas supply passage, the macroprojectile being constructed so as to have adhered thereto a plurality of microprojectiles having the foreign substance adsorbed thereon, the gas being controlled so as to accelerate the macroprojectile downwardly through said barrel at a high velocity, the macroprojectile being receivable into said cavity with an interference fit therewith and the microprojectiles being freely flowable through said narrow passage;

a sample holder disposed in said lower chamber for holding a sample of cells or tissue in vertical alignment with said one position of said table and said macroprojectile gun;

a passageway extending from the lower end of said narrow passage through said partition wall to provide a flow path so that macroprojectiles can move from said narrow passage through said passageway and thence to bombard the sample on said sample holder;

separate means for applying vacuum separately to said upper and lower chambers; and rotatable vacuum seal means disposed between said table and said partition so that said table can be rotated with respect to said partition and vacuum will be continuously maintained in said lower chamber.

6. Apparatus for injecting microprojectiles carrying DNA into living cells and tissue, comprising:

a housing defining an enclosure, said housing having an internal partition wall dividing the interior of said housing into an upper chamber and a lower chamber;

a pair of hingedly mounted doors for selectively and individually closing and hermetically sealing said chambers and releasable latches for releasably securing said doors in the closed position wherein said chambers are hermetically sealed;

a rotatable, circular table in said upper chamber, said table having a series of circumferentially spaced-apart, upwardly opening pockets therein and a macroprojectile stopper plug removably disposed in each of said pockets, said macroprojectile stopper plug having an enlarged central cavity which opens upwardly through the upper surface of said stopper and a narrow passage which extends from the bottom of said cavity through the bottom of said stopper plug and an opening in the bottom of each of said pockets;

a reciprocable, one-way pusher engageable with said table for effecting stepwise indexing movement of said pockets through a series of circumferentially spaced-apart positions, said table also having a series of spaced-apart alignment pin recesses in the periphery thereof, a reciprocable alignment pin receivable in one of said recesses and means for inserting said alignment pin into one of said alignment pin recesses so as to releasably lock said table in one of said positioning between indexing movements of said table;

a macroprojectile gun comprising an upright gun barrel extending upwardly from a position close to and located directly above one of said positions in vertical alignment with the macroprojectile stopper plug at said one position through said upper chamber to a location outside said housing, a breech block assembly mounted on the upper end of said barrel and having an internal bore constructed so as to hold a macroprojectile, a pivotally mounted breech block and latch means for releasably latching said breech block in a position so as to close the upper end of said internal bore, said breech block having a gas supply passage therethrough and communicating with the upper end of said internal bore, a supply of compressed gas and a valve in communication with said supply of compressed gas and said gas supply passage for controlling flow of gas from said supply through said gas supply passage, the macroprojectile being constructed so as to have adhered thereto a plurality of microprojectiles having DNA adsorbed thereon, the compressed gas being controlled so as to accelerate the macroprojectile downwardly through said barrel at a high velocity, the macroprojectile being receivable into said cavity in said macroprojectile stopper with an interference fit therewith and the microprojectiles being freely flowable through said narrow passage;

a sample holder disposed in said lower chamber for holding a sample of cells or tissue in vertical alignment with said one position of said table and said macroprojectile gun;

passageway means extending from the lower end of said narrow passage through said partition wall to provide a flow path so that microprojectiles can move from said narrow passage through said passageway and thence to bombard the sample on said sample holder;

separate means for applying vacuum separately to said upper and lower chambers; and vacuum seal means disposed between said table and said partition wall so that said table can be rotated with respect to said partition wall and vacuum will be continuously maintained in said lower chamber, said vacuum seal means comprising a seal plate disposed between the lower surface of said table and the upper surface of said partition wall, spring means resiliently urging said table against said seal plate and urging said seal plate against said partition wall, the contacting areas of said seal plate with the lower surface of said table having precisionfinished flat surfaces so as to seal said upper chamber from said lower chamber, said passageway means comprising a single passage through said seal plate in vertical alignment with said one position and a single orifice through said partition wall in vertical alignment with said single passage.

7. A method of injecting a foreign substance into a sample of plant cells or tissue utilizing a sample chamber for holding the sample, an injection chamber containing a movable transport member having a series of spaced-apart stopper plugs mounted thereon and movable therewith through a series of positions, a macroprojectile gun for directing a macroprojectile at one of said stopper plugs at one of said positions, passage means extending from said one stopper plug into said sample chamber, which method comprises:

maintaining a vacuum in both of said sample chamber and said injection chamber;

firing said macroprojectile gun to accelerate a macroprojectile carrying microprojectiles coated with said substance to said one stopper plug at said one position so that said macroprojectile abuts against and is sealed with respect to said stopper plug and said microprojectiles move at a high speed through said passage means and then bombard said sample chamber whereby said substance becomes lodged in the interior of the sample and when said macroprojectile seals against said one stopper plug, said passage means is closed after the microprojectiles have flowed therethrough into said sample chamber;

reloading said macroprojectile gun with another macroprojectile;

maintaining said injection chamber under vacuum;

while said injection chamber is under vacuum, shifting said transport member to bring a different one of said stopper plugs into said one position;

firing said macroprojectile gun again to bombard the sample with another quantity of microprojectiles that are coated with said substance;

continuously maintaining said sample chamber under a substantially constant vacuum during said firing steps; and isolating said sample chamber from said injection chamber except during the flow of microprojectiles into said sample chamber.

* * * * *

UNITED STATES PATENT AND TRADEMARK OFFICE
CERTIFICATE OF CORRECTION

PATENT NO. : 5 066 587
DATED : November 19, 1991
INVENTOR(S) : Lawrence Duane JONES et al It is certified that error appears in the above-identified patent and that said Letters Patent is hereby corrected as shown below:

Column 6, line 56; begin a new paragraph with "In a presently preferred embodiment..."

Column 10, line 31; change "precisionfinished" to ---precision-finished---.

Column 11, line 18; change "macroprojectiles" to ---microprojectiles---.

line 60; change "positioning" to ---positions---.

Signed and Sealed this

Twenty-seventh Day of April, 1993

*Attest:*

MICHAEL K. KIRK

*Attesting Officer*  Acting Commissioner of Patents and Trademarks